United States Patent
Eccleston

(10) Patent No.: US 7,588,549 B2
(45) Date of Patent: Sep. 15, 2009

(54) THERMOELECTRIC TEMPERATURE CONTROL FOR EXTRACORPOREAL BLOOD CIRCUIT

(75) Inventor: Rolando A. Eccleston, Ann Arbor, MI (US)

(73) Assignee: Terumo Cardiovascular Systems Corporation, Ann Arbor, MI (US)

(*) Notice: Subject to any disclaimer, the term of this patent is extended or adjusted under 35 U.S.C. 154(b) by 125 days.

(21) Appl. No.: 11/498,441

(22) Filed: Aug. 3, 2006

(65) Prior Publication Data

US 2008/0031773 A1 Feb. 7, 2008

(51) Int. Cl.
- *A61M 37/00* (2006.01)
- *B01J 19/00* (2006.01)
- *F28F 3/12* (2006.01)
- *F28F 1/00* (2006.01)
- *F28F 7/00* (2006.01)
- *A61C 5/06* (2006.01)
- *F25F 21/02* (2006.01)

(52) U.S. Cl. .............. 604/4.01; 604/6.13; 604/6.14; 604/93.01; 422/44; 165/168; 165/177; 165/185; 165/186; 62/3.2

(58) Field of Classification Search .......... 604/6.13, 604/6.14, 6.16, 4.01, 93.01, 65–67, FOR. 100; 165/DIG. 510, 263, 264, 278, 288, 289, 148, 165/164, 168, 177, DIG. 9, DIG. 228, DIG. 533; 62/3.2, 3.3, 3.6; 422/45, 46

See application file for complete search history.

(56) References Cited

U.S. PATENT DOCUMENTS

| | | | | |
|---|---|---|---|---|
| 3,140,716 A | * | 7/1964 | Harrison et al. | 607/106 |
| 3,640,283 A | * | 2/1972 | Bhatia et al. | 607/106 |
| 3,675,710 A | * | 7/1972 | Ristow | 165/111 |
| 3,731,731 A | * | 5/1973 | Kyvsgaard et al. | 165/46 |
| 3,927,981 A | * | 12/1975 | Viannay et al. | 422/48 |
| 3,998,593 A | * | 12/1976 | Yoshida et al. | 422/46 |

(Continued)

FOREIGN PATENT DOCUMENTS

EP 0445079 4/1991

(Continued)

OTHER PUBLICATIONS http://www.goodfellow.com/csp/active/static/A/Polymethylmethacrylate.HTML GoodFellow PMMA material information, including thermal conductivity. Accessed Jan. 30, 2008.*

(Continued)

*Primary Examiner*—Leslie Deak
*Assistant Examiner*—Adam Marcetich
(74) *Attorney, Agent, or Firm*—Gael Diane Tisack, Esq.; MacMillan, Sobanski & Todd, LLC

(57) ABSTRACT

A waterless blood heater/cooler device directly controlling temperature of blood flowing through an extracorporeal blood circuit. A thermoelectric module is coupled to a supply voltage to generate a temperature difference. A heat exchanger cassette comprising a core and first and second laminar flow guides is in thermal contact (directly or indirectly) with the thermoelectric module. The cassette has a plurality of tubes for carrying parallel channels of the blood. The first and second laminar flow guides provide an inlet and an outlet for coupling to the extracorporeal blood circuit and respective intermediate chambers for receiving respective ends of the tubes in order to guide the blood to and from respective tubes in a substantially laminar flow.

18 Claims, 7 Drawing Sheets

U.S. PATENT DOCUMENTS

| | | | |
|---|---|---|---|
| 4,047,562 A * | 9/1977 | Weber | 165/111 |
| 4,047,563 A * | 9/1977 | Kurata | 165/158 |
| 4,356,383 A * | 10/1982 | Dahlberg et al. | 392/470 |
| 4,440,722 A * | 4/1984 | Luppi | 422/46 |
| 4,476,685 A * | 10/1984 | Aid | 62/3.3 |
| 4,483,341 A * | 11/1984 | Witteles | 606/21 |
| 4,559,999 A * | 12/1985 | Servas et al. | 165/156 |
| 4,883,117 A * | 11/1989 | Dobbs et al. | 165/164 |
| 5,162,101 A * | 11/1992 | Cosentino et al. | 422/46 |
| 5,237,821 A * | 8/1993 | Okumura et al. | 62/3.2 |
| 5,860,470 A * | 1/1999 | Andersson et al. | 165/70 |
| 5,941,303 A | 8/1999 | Gowan et al. | |
| 6,673,098 B1 * | 1/2004 | Machold et al. | 607/96 |
| 6,729,389 B2 * | 5/2004 | Ohashi | 165/168 |
| 6,755,026 B2 | 6/2004 | Wallach | |
| 2001/0009610 A1 * | 7/2001 | Augustine et al. | 392/470 |
| 2004/0026068 A1 * | 2/2004 | Schmidt et al. | 165/46 |
| 2004/0079089 A1 * | 4/2004 | Wallach | 62/3.2 |
| 2004/0158191 A1 | 8/2004 | Samson et al. | |
| 2004/0190885 A1 * | 9/2004 | Entenman et al. | 392/470 |
| 2004/0238162 A1 * | 12/2004 | Seiler et al. | 165/148 |
| 2009/0018629 A1 * | 1/2009 | Yoshida et al. | 607/113 |

OTHER PUBLICATIONS http://en.wikipedia.org/wiki/Thermal_conductivity Online encyclopedia article on thermal conductivity, including value for water. Accessed Jan. 31, 2008.*

* cited by examiner ured manner. Typical
THERMOELECTRIC TEMPERATURE CONTROL FOR EXTRACORPOREAL BLOOD CIRCUIT

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to blood perfusion systems for cardiac surgery, and, more specifically, to a waterless blood heater/cooler.

Heating and cooling devices are an important part of blood perfusion systems used during cardiac surgery. During surgery, blood is cooled in a bypass circuit to induce hypothermia to protect the organs. A separate cardioplegia circuit typically provides a dedicated flow of cooled solution directly to the heart, at least periodically. When the surgery has been completed, the blood and/or other fluids flowing in the two circuits are heated prior to the patient waking from anesthesia. During various circumstances that may arise during operation of the blood perfusion system, it becomes desirable not only to heat both circuits or cool both circuits simultaneously, but also to cool one circuit while the other is heating or to deactivate one circuit while the other is either heating or cooling.

Conduits carrying the blood and/or cardioplegia in each circuit pass through respective heat exchangers in order to perform heating or cooling in a controlled manner. Typical prior art systems use water or other heat exchange fluids passing through the heat exchangers thermally coupled to passages carrying the blood for adding heat to or removing heat from the blood/cardioplegia as necessary. An integrated heater/cooler unit having an integrated controller and an integrated power supply usually includes a single ice-bath compartment for selectably cooling the water in both water circuits and a pair of heating devices for selectably heating the water in the two circuits independently.

The size of a heat exchanger that is required is proportional to the efficiency of the heat exchange. Lower efficiency results in a larger heat exchanger and, consequently, a greater volume of blood is present within it. It is desirable to reduce the blood volume (priming volume) present within the perfusion system. Therefore, it would be desirable to increase the heating/cooling efficiency as well as improving temperature stability and reducing the cycle time when a new target temperature is commanded.

Prior art heater/coolers depending upon an ice bath for cooling require efforts to obtain the ice and to prepare the unit for operation. Once prepared, the heater/cooler unit must be used within a certain amount of time. Furthermore, the use of an ice bath and the pumps and conduits for carrying the heat exchange fluid are significant. The heater/cooler is usually contained within a separate cart, and space must be available in an operating room to accommodate it. Due to the large size of the equipment, it is not easily integrated with other operating room equipment. Thus, it would be desirable to reduce the size of equipment.

Heater used in previous blood heater/coolers are typically comprised of electrically resistive heating elements. A relatively high voltage has been required in order to provide the necessary heating characteristics. Because of the presence of the high voltage, safety measures to protect the patient and the users of the equipment must be taken which add expense to the equipment. Furthermore, the power requirements may exceed the available power from typical convenience outlets. Thus, it would be desirable to reduce the power requirements.

The use of purified water as a heat exchange fluid has associated maintenance requirements due to the potential for water induced corrosion and bacterial growth. The constant maintenance is costly and troublesome.

SUMMARY OF THE INVENTION

The present invention utilizes a waterless heat exchange system employing a novel heat exchange cassette and a thermoelectric heater/cooler element to achieve advantages of increased efficiency, reduced blood volume, reduced equipment size, increased safety, reduced power requirements, and increased reliability. The waterless thermoelectric device is small enough to fit on an APS1 base, a pole, or the surgical table. It provides large heating and cooling capabilities, substantially instantaneous change of temperature with no moving parts, and operates at low voltage DC.

In one aspect of the invention, a device is provided for directly controlling temperature of blood flowing through an extracorporeal blood circuit. A thermoelectric module is coupled to a supply voltage to generate a temperature difference. A heat exchanger cassette comprising a core and first and second laminar flow guides is in thermal contact (directly or indirectly) with the thermoelectric module. The cassette has a plurality of tubes for carrying parallel channels of the blood. The first and second laminar flow guides provide an inlet and an outlet for coupling to the extracorporeal blood circuit and respective intermediate chambers for receiving respective ends of the tubes in order to guide the blood to and from respective tubes in a substantially laminar flow.

DETAILED DESCRIPTION OF PREFERRED EMBODIMENTS

Figure 1:
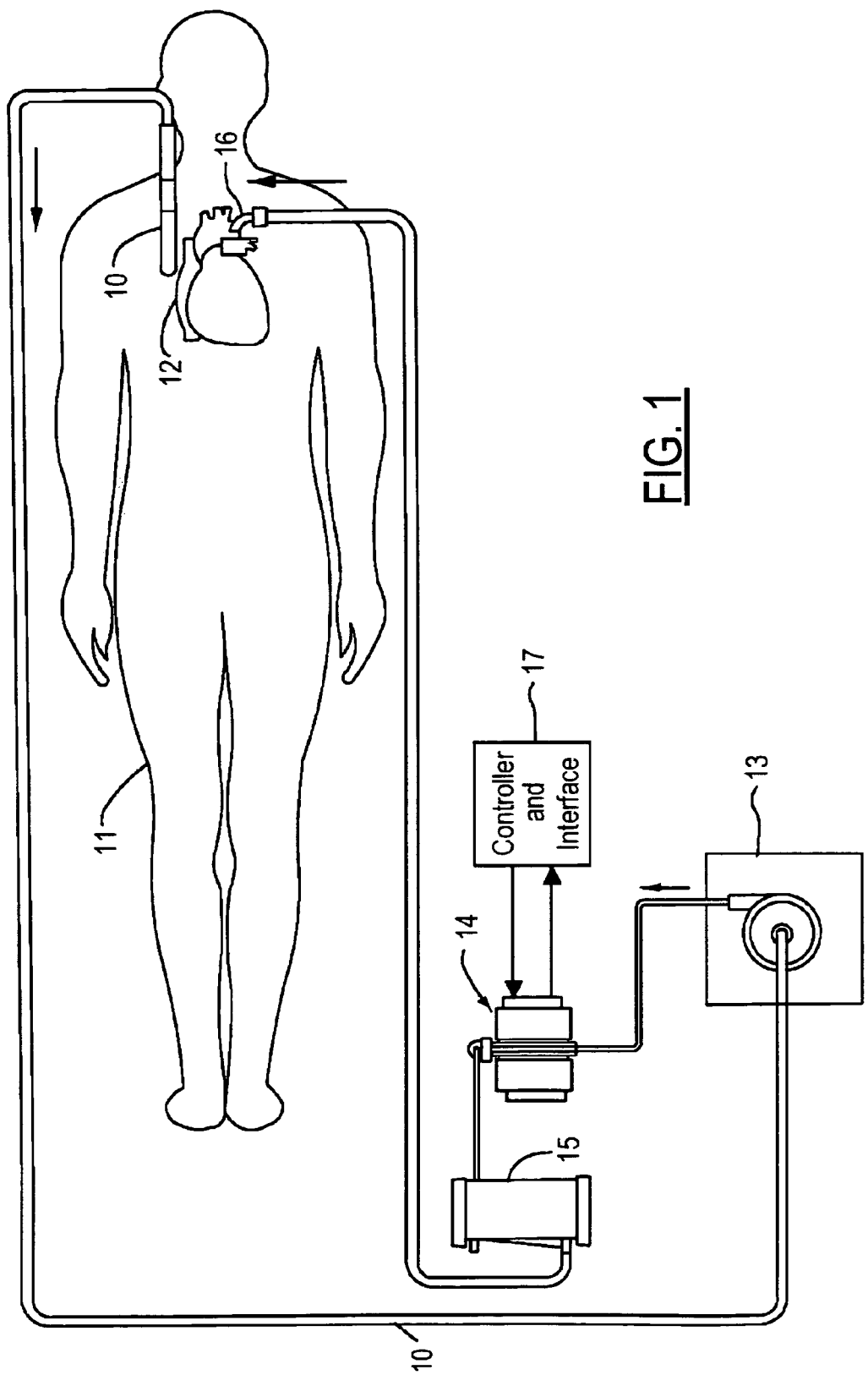
FIG. 1 is a simplified diagram of a perfusion system.

FIG. 1 shows a simplified diagram of a perfusion system for supporting on-pump coronary artery bypass graft surgery. A venous catheter 10 is inserted into a patient 11 to remove blood at a suitable point such as the superior or inferior vena cava 12. Venous blood is driven by an arterial pump 13 which may be comprised of a centrifugal or roller pump, for example. Blood passes through a heater/cooler device 14 and then to an oxygenator 15. Oxygenated blood is conducted to an arterial cannula 16 for return to the patient's aorta. A controller and interface 17 is connected to heater/cooler 14 to allow a medical technician to selectably control the temperature of blood flowing in the perfusion circuit and/or the temperature of a cardioplegia solution.

The heater/cooler device of the present invention utilizes thermoelectric modules as the source of heating and cooling. Thermoelectric devices comprise two ceramic substrates disposed on opposite sides of semiconductor materials comprising individual "couples" having P-type and N-type regions connected in series. The P-type and N-type regions are typically doped with bismuth telluride. Direct electrical current flowing through the device causes the P-type material to act as a hot junction needing to be cooled and the N-type material as a cold junction needing to be heated, thereby creating a temperature differential across the device that results from the Peltier Effect. One ceramic substrate becomes hotter than the ambient temperature while the other ceramic substrate becomes colder than the ambient temperature. By changing polarity of the current, the hot and cold substrates can be switched.

A typical thermoelectric module can produce a temperature differential of about 67° C. Typical target temperatures needed for blood perfusion applications ranges from about 15° C. to about 38°. Thus, thermoelectric modules alone can provide the desired heating and cooling when ambient temperature is not above about 34° C. (provided they have sufficient heat capacity for the volumes of blood to be handled). More preferably, additional heat dissipation is provided using heat sinks or other means for controlling the ambient temperature seen by the thermoelectric modules.

Figure 2:
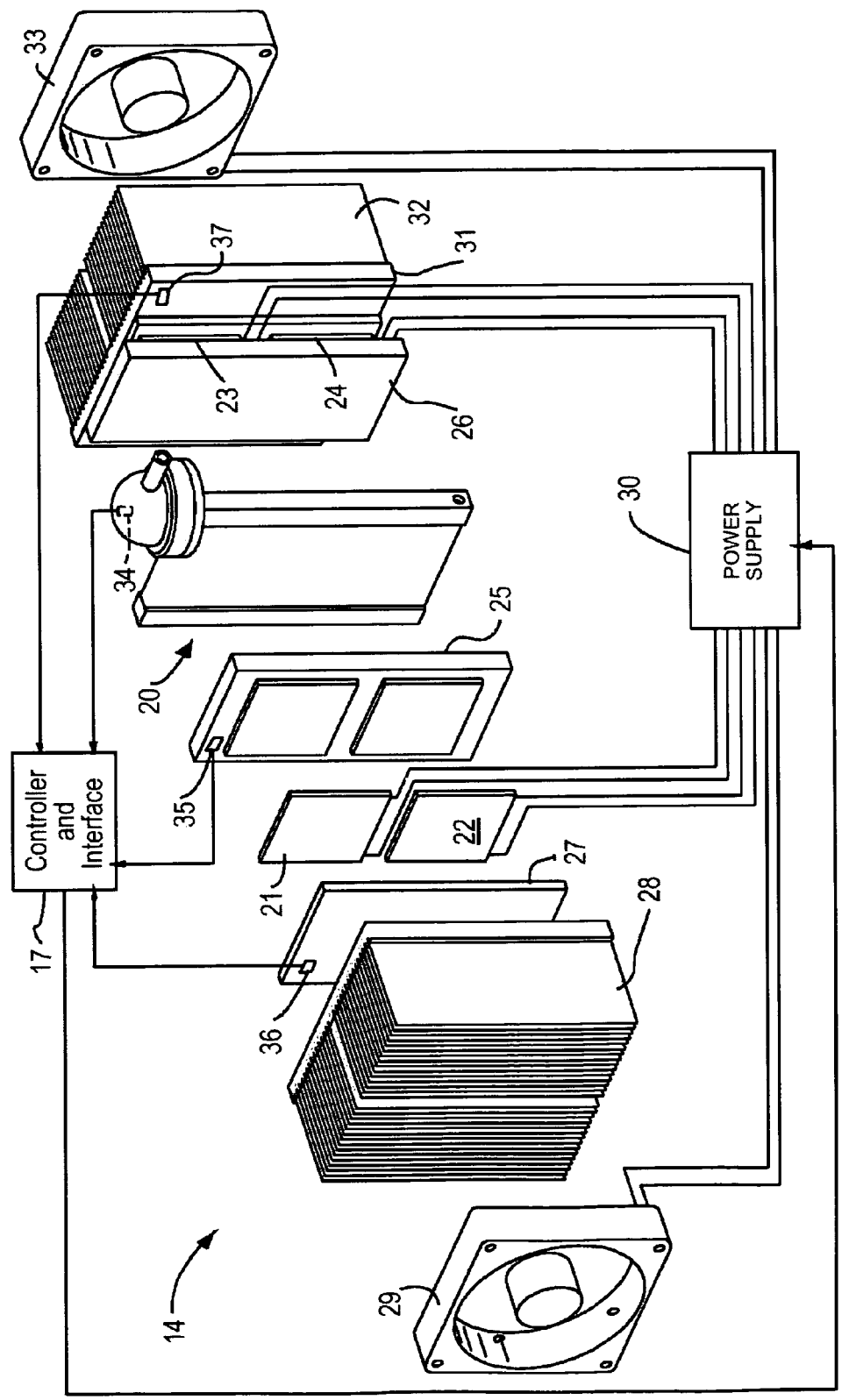
FIG. 2 is an exploded, perspective view of one preferred embodiment of the heater/cooler device of the present invention.

A preferred embodiment of the heater/cooler device 14 is shown in FIG. 2. A heat exchanger cassette 20 receives a flow of blood and/or cardioplegia solution which is to be heated or cooled by thermoelectric modules 21-24. Temperature transfer blocks 25 and 26 are placed between thermoelectric modules 21-24 and cassette 20, respectively, and are preferably comprised of solid aluminum for efficient transfer of heat between cassette 20 and thermoelectric modules 21-24. Transfer blocks 25 and 26 are preferably smooth on their sides facing cassette 20 and may preferably include raised sections for receiving the thermoelectric modules on their opposite sides.

In order to carry away heat during a cooling operation (thereby lowering the ambient temperature of the thermoelectric modules), temperature dissipation blocks 27 and 31 and finned heat sinks 28 and 32 are thermally coupled to the opposite sides of thermoelectric modules 21-24. Fans 29 and 33 may also be provided to increase the efficiency of removing heat from the heat sinks.

A power supply 30 provides a DC voltage to thermoelectric modules 21-24 as commanded by controller and interface 17. Power supply 30 also powers fans 29 and 33. A plurality of temperature sensors 34-37 are connected to controller and interface 17 for monitoring the temperature at various points in the heater/cooler system. A blood temperature sensor 34 is contained within cassette 20, while the other temperature sensors are installed in different key locations to provide feedback information that allows controller 17 to insure safe and efficient operation of the entire system.

The temperature differential of the thermoelectric modules can be controlled in response to either the supplied voltage or the supplied current. In a preferred embodiment, the present invention controls the current supplied to the thermoelectric modules because current usage is a more critical parameter in medical systems of this type.

In the system of FIG. 2, cassette 20 would be a disposable device (i.e., used for only one surgical procedure) and the remaining components would be reusable. In operation, controller 17 would run a diagnostic routine to insure that the system is operating properly on power-up. Following the diagnostic routine, the controller would process input commands provided from the user through the interface (e.g., a keyboard). The user would be prompted to insert the heat exchange cassette and to configure the system accordingly. The system can automatically secure the cassette in place with an auto-loading device (not shown) or be manually secured by the user. With the cassette in place and the system initialized, driver circuits to the thermoelectric modules would be enabled. For example, a command is sent to a current control loop circuit which converts the command into a current supplied to the thermoelectric modules. A sample of the current is fed back to the control loop of the controller together with temperature measurements from the various sensors. Based on a target temperature set by the user, the controller adjusts current supplied to the thermoelectric modules to achieve and maintain the target temperature.

Figures 3, 4:
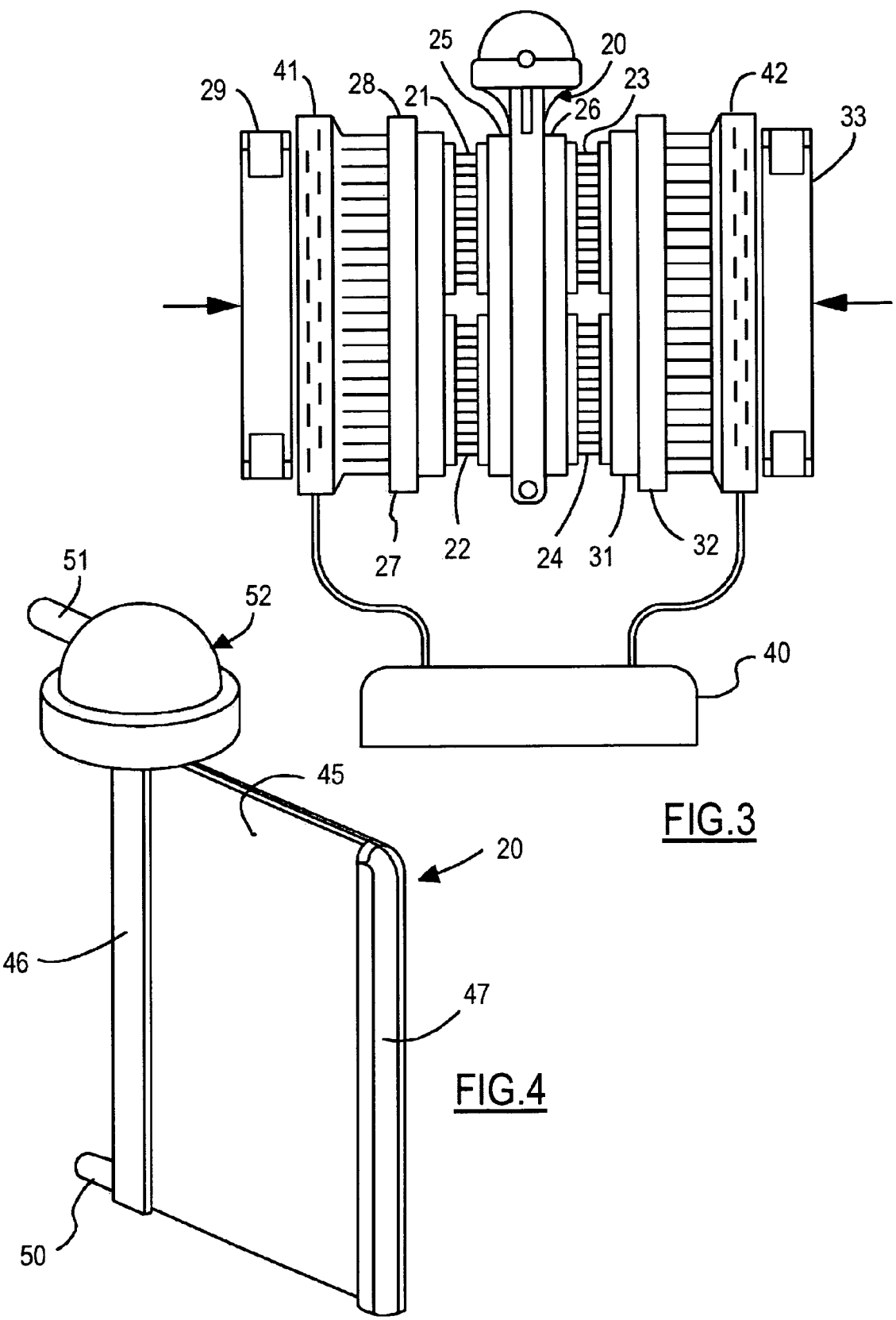
FIG. 3 is a front, plan view of another embodiment of the heater/cooler device.
FIG. 4 is a rear, perspective view of the heat exchange cassette of FIGS. 2 and 3.

Increased cooling can be achieved by further lowering the ambient temperature seen by the thermoelectric modules. In FIG. 3, active cooling of the heat sinks is obtained using a compressor 40 and evaporators 41 and 42 for actively cooling the fins and heat sink. The flow of cold air across the heat sink further improves the efficiency of heat removal from the thermoelectric system. Fans 29 and 33 force air through the evaporators for cooling and then onto the fins to draw heat out of heat sinks 28 and 32. Other possible configurations include placing the evaporators at other orientations or removing the heat sink entirely and coupling the evaporators directly to temperature dissipation blocks 27 and 31, with or without fans. Thermal insulation (not shown) should be used around the various reusable components in order to minimize thermal coupling between the cold and hot sides of the device. Heat exchanger cassette 20 is preferably retained between temperature transfer blocks 25 and 26 under light pressure to provide a good surface-to-surface connection for maximizing thermal transfer efficiency.

Figure 5:
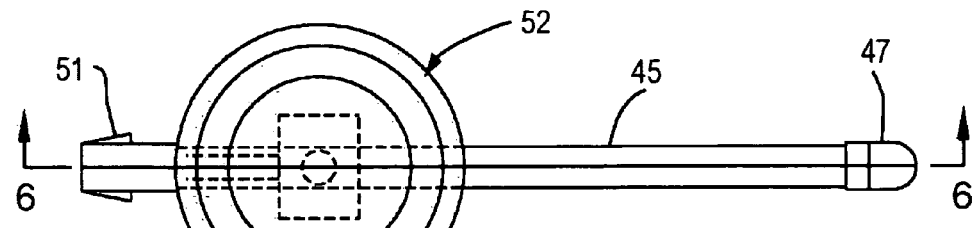
FIG. 5 is a top view of the heat exchange cassette of FIG. 4.
Figure 6:
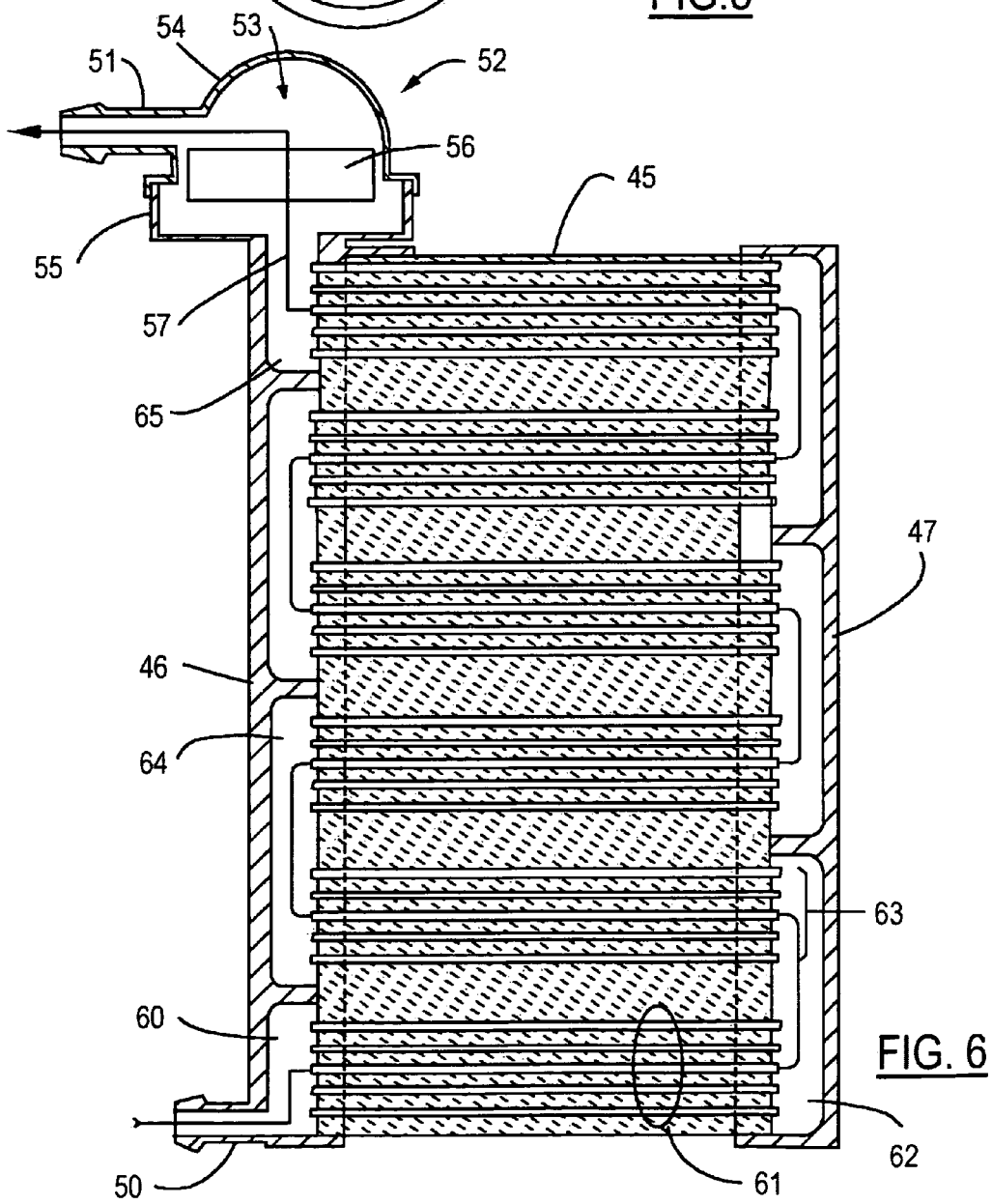
FIG. 6 is a cross section along line 6-6 of FIG. 5.

FIGS. 4-6 show heat exchange cassette 20 in greater detail. A core 45 has laminar flow guides 46 and 47 along each lateral edge. Flow guides 46 and 47 are preferably molded from a biocompatible thermoplastic. An inlet 50 and an outlet 51 are associated with laminar flow guide 46 together with a bubble trap 52. Inlet 50 and outlet 51 include barbed fittings for attaching conventional tubing used for carrying perfused blood. During operation, blood or cardioplegia fluid circulates from inlet 50 through an inlet chamber within laminar flow guide 46 into a multi-channel cell that feeds the blood/fluid across core 45 to laminar glow guide 47 where it follows another chamber into further multi-channel cells flowing back and forth between flow guides 46 and 47 until it reaches an outlet chamber coupled through bubble trap 52 to outlet 51. Thus, the blood or fluid passes across core 45 multiple times to increase the amount of time that its temperature is influenced by the device.

As shown in FIG. 6, bubble trap 52 has an interior chamber 53 defined by a cover 54 and a base 55 for containing a conventional blood filter 56. Flow guides 46 and 47 have chambers for directing blood/fluid flow within respective lateral sides of the flow guides. A blood flow 57 zig-zags through core 45 as shown. Flow 57 enters an input chamber 60 via inlet 50 and enters a first multi-channel cell 61. After flowing across core 45, the blood flow reverses direction while flowing through an intermediate chamber 62 in flow guide 47 and then enters a second multi-channel cell 63 for re-traversing core 45 to an intermediate chamber 64 in flow guide 46. After additional traversals, blood flow 57 enters an outlet chamber 65 which is open to bubble trap 52 and outlet 51.

Figure 7:
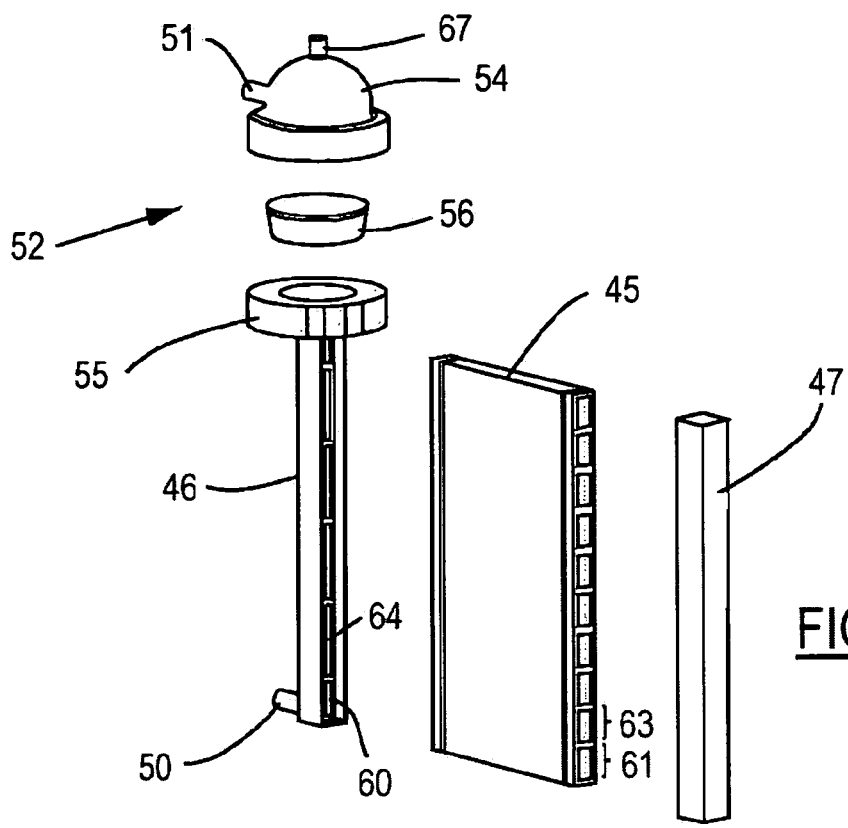
FIG. 7 is an exploded view of the heat exchange cassette of FIG. 4.

As shown in FIG. 7, cells such as 61 and 63, in core 45 comprise groups of thin tubes or channels spaced within the core. Bubble trap 52 may also include a port 67 for removing gases collected by bubble trap 52 and/or for mounting a temperature sensor to monitor the heating or cooling of the blood.

Figure 8:
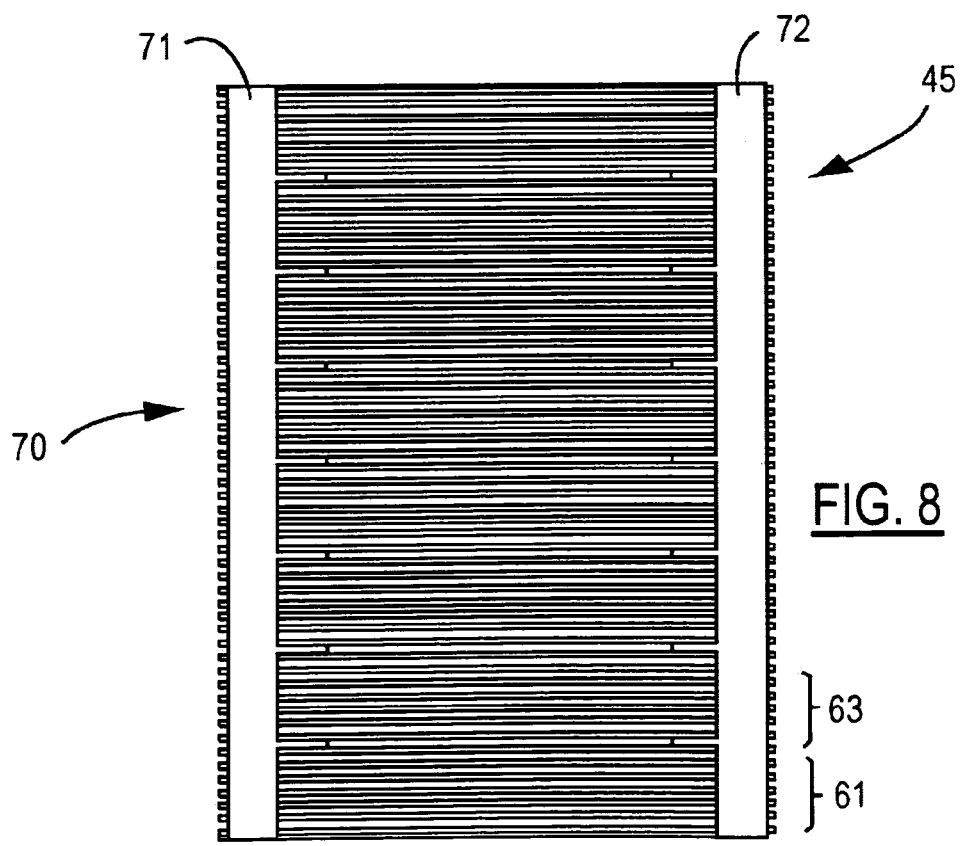
FIG. 8 is a perspective view of the tube assembly.
Figure 9:
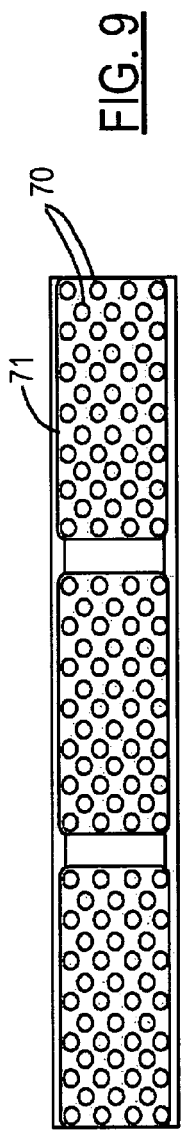
FIG. 9 is a cross section of a portion of the tube assembly.

As shown in greater detail in FIG. 8, core 45 comprises cells each having respective tubes 70 arranged side by side in each cell to carry blood flow across the core. Tubes 70 are encapsulated within a thermal transfer matrix which preferably includes integral sealing collars 71 and 72 at respective sides. FIG. 9 shows a portion of the core in cross-section. Tubes 70 preferably comprise cylindrical steel tubes that are grouped and organized in parallel having a staggered formation to increase efficiency of heat exchange. In one preferred embodiment, the steel tubes each have an inner diameter of about 0.029 inches, an outer diameter of about 0.042 inches, and a length of about 4 inches. In order to accommodate a typical flow volume, approximately 47 tubes are contained within each cell. The thermal transfer matrix may preferably include a polymer or thermally conductive resin embedding tubes 70. Preferably, the matrix is electrically insulative. Although any suitable polymer providing high thermal conductivity and high electrical resistivity can be used, one preferred embodiment employs a thermally conductive silicone adhesive, product number 5405, available from Loctite which has a thermal conductivity of about 0.060 W/mK and a volume resistivity of $4.0 \times 10^{14}$ ohms. The higher the thermal conductivity the better the transfer efficiency and the less spacing that will be required between adjacent tubes. Use of a fluid instead of a solid material may achieve a higher thermal conductivity of 0.065 W/mK as will be described below.

Figure 10:
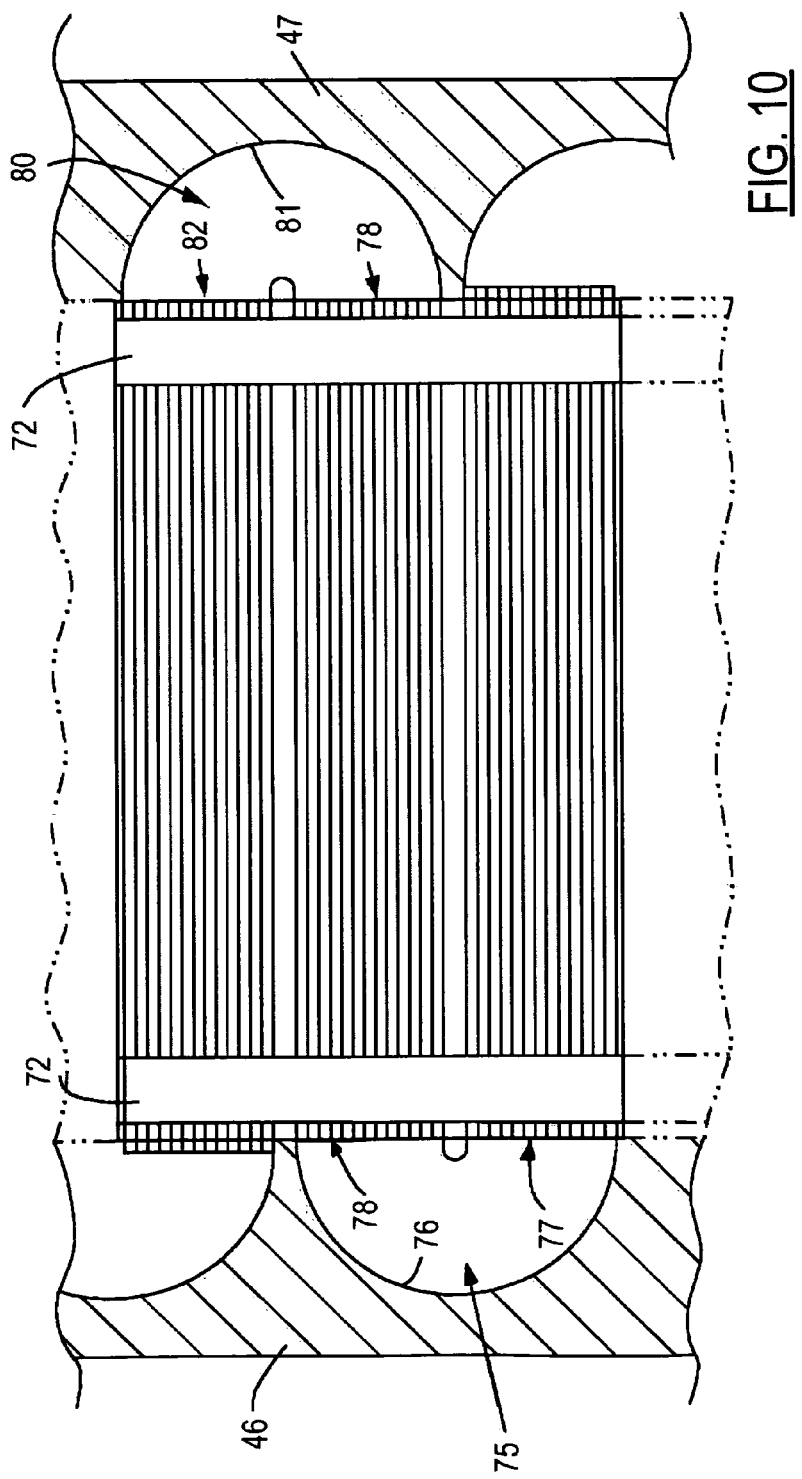
FIG. 10 is a cross section of a portion of the tube assembly and the laminar flow guides.

FIG. 10 is a cross-section showing an embodiment wherein the intermediate chambers within the laminar flow guides are characterized by radially curved outside walls. Thus, an intermediate chamber 75 includes an outside radially curving wall 76 for reversing direction of the substantially laminar flow of blood leaving a cell 77 and entering a cell 78. Likewise, an intermediate chamber 80 has an outside wall 81 which is radially curved to reverse the direction of laminar blood flow from cell 78 to a cell 82. Preferably, walls 76 and 81 have a radius of substantially 180°. It is desired to avoid turbulence in the blood flow because turbulence leads to hemolysis. By providing a smooth laminar fluid flow around each bend, such damage to the blood cells is prevented.

Figure 11:
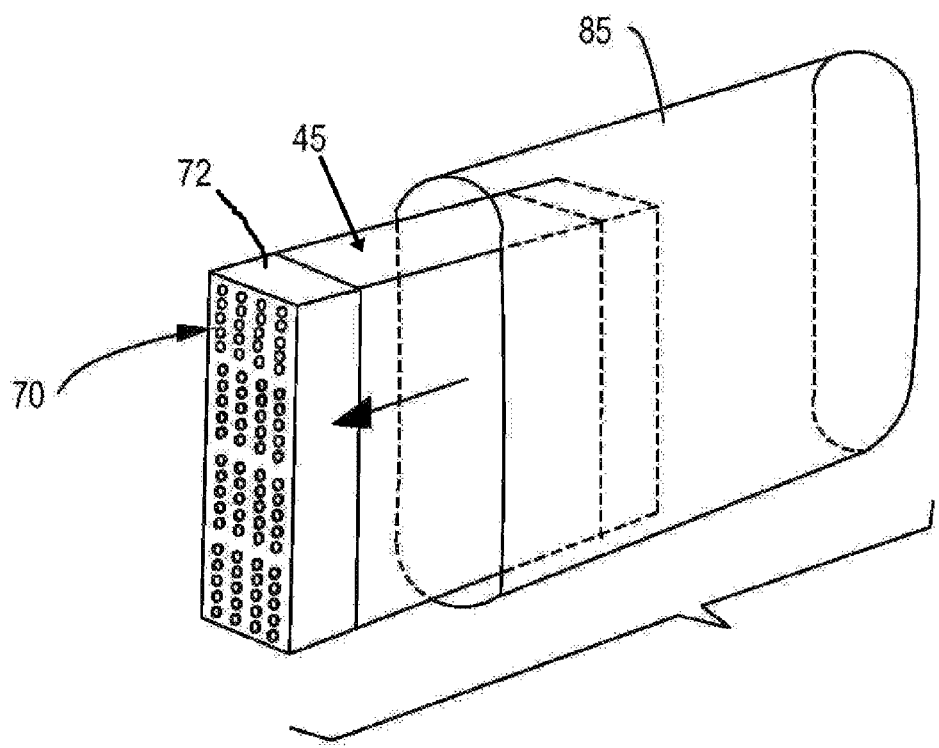
FIG. 11 illustrates the assembly of a flexible bag over the tube assembly.
Figure 12:
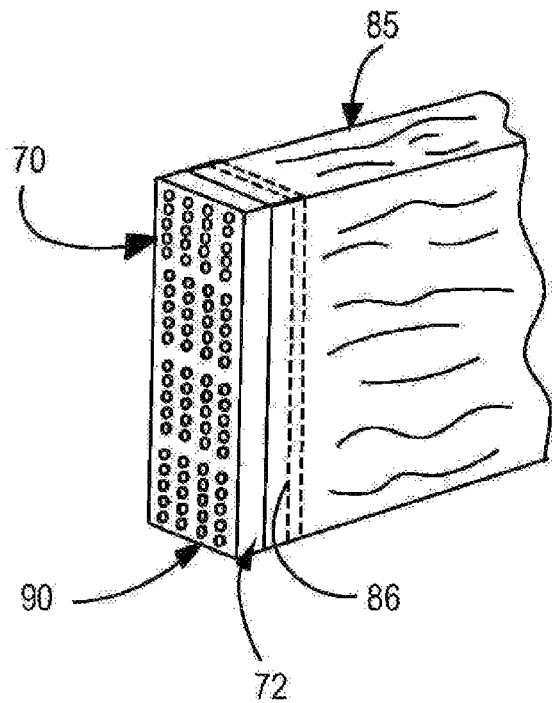
FIG. 12 shows the flexible bag welded to the tube assembly to retain a non-circulated coupling fluid.

Rather than being embedded in a continuous block of solid polymer as shown in FIG. 9, a high performance heat transfer fluid contained within a flexible bag can be employed as shown in FIGS. 11 and 12. In order to align the stainless steel tubes, sealing collars 72 may be part of solid fixing blocks at opposite ends of the core. For example, a block 90 shown in FIG. 12 may be formed around tube 70 in a conventional potting process. When potting the ends of the stainless tubes into a molded plastic material, it may be desirable to trim the ends after potting to ensure that all tubes are open for blood circulation.

Flexible thermally conductive bag 85 has a cylindrical shape with a diameter sufficient to receive core 45. After attaching to one of the collars 72, the interior of bag 85 is filled with the thermally conductive fluid and then the remaining side of bag 85 is sealed to the other collar 72. As shown in FIG. 12, the attachment between bag 85 and collar 72 preferably includes a weld 86. If block 90 comprises a thermoconductive plastic material, then the flexible bag may be ultrasonically welded at 86. Alternatively, block 90 may be a metal block having holes pre-drilled for receiving stainless steel tubes 70 in a sealed matter (such as press fit). In that case, a laser weld could be used to join flexible bag 85 to metallic block 90.

After joining and filling of the bag together with any trimming of the stainless steel tubes and fixing blocks, the core is inserted into the chambers within the laminar flow guides and is sealed in any conventional manner.

Bag 85 may be comprised of the same types of materials used for cardiotomies in blood perfusion systems. A heat exchange fluid such as the 7000 series (part number HFE-7500) available from 3M can be used, having a thermal conductivity of about 0.065 W/mK and a volume resistivity of about $2 \times 10^8$ ohm-cm.

What is claimed is:

1. A device for directly controlling temperature of blood flowing through an extracorporeal blood circuit, comprising:
    a thermoelectric module for coupling to a supply voltage to generate a temperature difference; and
    a heat exchanger cassette comprising a core and first and second laminar flow guides, wherein the core is in thermal contact with the thermoelectric module and has a plurality of tubes for carrying parallel channels of the blood, wherein the first and second laminar flow guides provide an inlet and an outlet for coupling to the extracorporeal blood circuit, wherein the tubes are grouped into respective multi-tube cells, wherein all the tubes in any particular multi-tube cell carry the blood in parallel and in the same direction, wherein the first and second laminar flow guides include respective intermediate chambers for receiving respective ends of the tubes in order to connect the multi-tube cells in series between the inlet and the outlet, wherein each intermediate chamber carries a combined flow from one multi-tube cell to a following multi-tube cell, wherein the intermediate chambers each include a radially-curved outside wall for reversing the direction of flow from one multi-tube cell to the next while maintaining a substantially laminar flow, wherein a thermal transfer matrix encapsulates the tubes and provides a thermally conductive path between the tubes and the thermoelectric module, and wherein the thermal transfer matrix is an electrical insulator.

2. The device of claim 1 wherein the radially-curved outside walls each comprises an arc of substantially 180°.

3. The device of claim 1 wherein the thermal transfer matrix is comprised of a polymer embedding the tubes, the polymer having a thermal conductivity of about 0.060 W/mK or greater.

4. The device of claim 1 wherein the thermal transfer matrix is comprised of a heat transfer fluid retained in a flexible bag, the heat transfer fluid having a thermal conductivity of about 0.065 W/mK or greater.

5. The device of claim 1 further comprising a bubble trap integrated with the outlet.

6. The device of claim 5 wherein the bubble trap includes a filter.

7. The device of claim 5 further comprising a temperature sensor mounted to the bubble trap.

8. The device of claim 1 wherein the laminar flow guides are each comprised of a molded body having the intermediate chambers formed in one lateral side.

9. The device of claim 8 wherein one of the molded bodies includes the inlet formed as a barb fitting.

10. The device of claim 8 wherein one of the molded bodies includes the outlet formed as an outlet chamber receiving a bubble trap.

11. The device of claim 1 further comprising a metallic heat transfer plate disposed between the thermoelectric module and the heat exchanger cassette.

12. The device of claim 11 further comprising a second thermoelectric module and a second metallic heat transfer plate disposed between the second thermoelectric module and the heat exchanger cassette.

13. The device of claim 12 further comprising first and second thermal dissipation blocks disposed against the sides of the first and second thermoelectric modules opposite the first and second metallic heat transfer plates, respectively.

14. The device of claim 13 further comprising first and second finned heat sinks disposed against the first and second dissipation blocks, respectively.

15. The device of claim 13 further comprising a plurality of temperature sensors measuring temperatures at respective points on the device coupled to an electronic controller for supplying the voltage according to a desired temperature of the blood.

16. A blood perfusion system for coupling to a patient during cardiac surgery, comprising:
an inlet line carrying blood removed from the patient;
an return line carrying blood from the perfusion system back to the patient;
a pump for circulating blood from the inlet line to the return line;
an oxygenator coupled between the inlet line and the return line for oxygenating the blood; and
a heater/cooler coupled between the inlet line and the return line in series with the oxygenator, the heater/cooler comprising:
a thermoelectric module for coupling to a supply voltage to generate a temperature difference; and
a heat exchanger cassette comprising a core and first and second laminar flow guides, wherein the core is in thermal contact with the thermoelectric module and has a plurality of tubes for carrying parallel channels of the blood, wherein the first and second laminar flow guides provide an inlet and an outlet for coupling to the extracorporeal blood circuit, wherein the tubes are grouped into respective multi-tube cells, wherein all the tubes in any particular multi-tube cell carry the blood in parallel and in the same direction, wherein the first and second laminar flow guides include respective intermediate chambers for receiving respective ends of the tubes in order connect the multi-tube cells in series between the inlet and the outlet, wherein each intermediate chamber carries a combined flow from one multi-tube cell to a following multi-tube cell, wherein the intermediate chambers each include a radially-curved outside wall for reversing the direction of flow from one multi-tube cell to the next while maintaining a substantially laminar flow, wherein a thermal transfer matrix encapsulates the tubes and provides a thermally conductive path between the tubes and the thermoelectric module, and wherein the thermal transfer matrix is an electrical insulator.

17. A device for directly controlling temperature of blood flowing through an extracorporeal blood circuit, comprising:
a thermoelectric module for coupling to a supply voltage to generate a temperature difference; and
a heat exchanger cassette comprising a core and first and second laminar flow guides at first and second ends of the core, wherein the core has first and second sealing collars at the first and second ends for receiving the first and second laminar flow guides, respectively, wherein the core is in thermal contact with the thermoelectric module and has a plurality of spaced tubes for carrying parallel channels of the blood, wherein the first and second laminar flow guides provide an inlet and an outlet for coupling to the extracorporeal blood circuit, wherein the tubes are grouped into respective multi-tube cells, wherein all the tubes in any particular multi-tube cell carry the blood in parallel and in the same direction, wherein the first and second laminar flow guides include respective intermediate chambers for receiving respective ends of the tubes in order to connect the multi-tube cells in series between the inlet and the outlet, wherein each intermediate chamber carries a combined flow from one multi-tube cell to a following multi-tube cell, wherein the intermediate chambers each include a radially-curved outside wall for reversing the direction of flow from one multi-tube cell to the next while maintaining a substantially laminar flow, wherein a thermal transfer matrix fills the space between the tubes and encapsulates the tubes to provide a thermally conductive path between the tubes and the thermoelectric module, and wherein the thermal transfer matrix is an electrical insulator.

18. The device of claim 17 wherein the thermal transfer matrix is comprised of a heat transfer fluid retained in a flexible bag, wherein the flexible bag is sealed to the first and second sealing collars, the heat transfer fluid having a thermal conductivity of about 0.065 W/mK or greater.

* * * * *